US012661356B2

(12) United States Patent
Hasako et al.

(10) Patent No.: US 12,661,356 B2
(45) Date of Patent: Jun. 23, 2026

(54) L718 AND/OR L792 MUTANT TREATMENT-RESISTANT EGFR INHIBITOR

(71) Applicant: TAIHO PHARMACEUTICAL CO., LTD., Tokyo (JP)

(72) Inventors: Shinichi Hasako, Tsukuba (JP); Takao Uno, Tsukuba (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 963 days.

(21) Appl. No.: 17/309,847

(22) PCT Filed: Dec. 27, 2019

(86) PCT No.: PCT/JP2019/051377
§ 371 (c)(1),
(2) Date: Jun. 23, 2021

(87) PCT Pub. No.: WO2020/138400
PCT Pub. Date: Jul. 2, 2020

(65) Prior Publication Data

US 2022/0072000 A1 Mar. 10, 2022

(30) Foreign Application Priority Data

Dec. 28, 2018 (JP) ................................ 2018-247131

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC .............................. A61K 31/519; A61P 35/00
See application file for complete search history.

(56) References Cited

U.S. PATENT DOCUMENTS

| | | | |
|---|---|---|---|
| 2016/0194332 A1 | 7/2016 | Uno et al. |
| 2017/0101414 A1 | 4/2017 | Uno et al. |
| 2019/0262345 A1 | 8/2019 | Miyadera et al. |

FOREIGN PATENT DOCUMENTS

| | | | | |
|---|---|---|---|---|
| CA | 2922077 | | * | 2/2015 |
| CA | 29922077 | A1 | * | 2/2015 |
| EP | 3 037 424 | A1 | | 6/2016 |
| JP | WO2015/025936 | A1 | | 2/2015 |
| WO | WO 2015/175632 | A1 | | 11/2015 |
| WO | WO 2018/079310 | A1 | | 5/2018 |

OTHER PUBLICATIONS

Bersanalli et al. "L718Q Mutation as New Mechanism of Acquired Resistance to AZD9291 in EGFR-Mutated NSCLC" Journal of Thoracic Oncology vol. 11 No. 10: pp. 121-123, 2016 (Year: 2016).*
Mc Kim et al. "Dimethyl Sulfoxide USP, PhEur in Approved Pharmaceutical Product and Medical Devices" (Pharmaceutical Technology May 2, 2008, vol. 35, Issue 5 (Year: 2008).*
Written Opinion of the International Searching Authority issued Apr. 8, 2020 in PCT/JP2019/051377, 6 pages.
International Search Report issued Apr. 8, 2022 in PCT/JP2019/051377, 4 pages.
Japanese Office Action issued Jan. 10, 2023 in Japanese Patent Application No. 2021-530234 (with English translation), 7 pages.
Wei et al., "Three new disease-progression modes in NSCLC patients after EGFR-TKI treatment by next-generation sequencing analysis", Lung Cancer, 2018, vol. 125, pp. 43-50, XP085524020.
Lacouture "Mechanisms of cutaneous toxicities to EGFR inhibitors", Nature Reviews, Cancer, 2006, vol. 6, pp. 803-812.
Chong et al., "The quest to overcome resistance to EGFR-targeted therapies in cancer", Nature Medicine, 2013, vol. 19, No. 11, pp. 1389-1400.
Sharma et al., "Epidermal growth factor receptor mutations in lung cancer", Nature Reviews, Cancer, 2007, vol. 7, pp. 169-181.
Yang et al., "Investigating Novel Resistance Mechanisms to Third-Generation EGFR Tyrosine Kinase Inhibitor Osimertinib in Non-Small Cell Lung Cancer Patients", Clinical Cancer Research, 2018, vol. 24, No. 13, pp. 3097-3107.
Hasako et al., "TAS6417, A Novel EGFR Inhibitor Targeting Exon 20 Insertion Mutations", Molecular Cancer Therapeutics, 2018, vol. 17, No. 8, pp. 1648-1658.
Piotrowska Z. et al., "Preliminary Safety and Activity of CLN-081 in NSCLC with EGFR Exon 20 Insertion Mutations (Ins20)", EMSO2020 Poster, 2020, 1 page.
Piotrowska Z. et al., "Abstract 9077: Safety and activity of CLN-081 (TAS6417) in NSCLC with EGFR Exon 20 insertion mutations (Ins20)", ASCO Poster, 2021, 5 pages.
Sagara, et al., "Drug Discovery Transformation to Counquer Cancer" Medchem News, 2024, 34(4) 191-197.
Science Academy of Tsukuba, Aug. 2024, No. 43 (26 pages).
Nishio et al., "REZILIENT3: P3 study of zipalertinib plus chemo in NSCLC patients harboring EGFR ex20ins mutations", slides(O39-6), The 65th Annual Meeting of the Japan Lung Cancer Society, 2024.
Nishio et al., "REZILIENT3: P3 study of zipalertinib plus chemo in NSCLC patients harboring EGFR ex20ins mutations", abstract(O39-6), The 65th Annual Meeting of the Japan Lung Cancer Society 2024.

(Continued)

*Primary Examiner* — Marcos L Sznaidman
(74) *Attorney, Agent, or Firm* — Oblon, McClelland, Maier & Neustadt, L.L.P.

(57) ABSTRACT

The present invention provides an antitumor agent for treating a malignant tumor patient expressing EGFR having at least one mutation selected from the group consisting of L718X mutation in exon 18 and L792X mutation in exon 20, wherein X represents an arbitrary amino-acid residue, the antitumor agent comprising(S)—N-(4-amino-6-methyl-5-(quinolin-3-yl)-8.9-dihydropyrimido[5.4-b]indolizin-8-yl) acrylamide (Compound (A)) or a salt thereof.

6 Claims, 1 Drawing Sheet

Specification includes a Sequence Listing.

(56) References Cited

OTHER PUBLICATIONS

Yu, et al., "REZILIENT3: Phase 3 study of zipalertinib plus chemotherapy in patients with previously untreated, advanced nonsquamous non-small cell lung cancer (NSCLC) harboring epidermal growth factor receptor (EGFR) exon 20 insertions (ex20ins) mutations", Abstract(TPS8671), ASCO 2024.
Yu, et al., "REZILIENT3: Phase 3 study of zipalertinib plus chemotherapy in patients with previously untreated, advanced nonsquamous non-small cell lung cancer (NSCLC) harboring epidermal growth factor receptor (EGFR) exon 20 insertions (ex20ins) mutations", Poster(TPS8671), ASCO 2024.
Yu et al.," REZILIENT2: Phase 2 study of zipalertinib in patients with advanced non-small cell lung cancer (NSCLC) with exon 20 insertions (ex20ins) and other uncommon epidermal growth factor receptor (EGFR) mutations", Abstract(TPS8670), ASCO 2024.
Yu et al.," REZILIENT2: Phase 2 study of zipalertinib in patients with advanced non-small cell lung cancer (NSCLC) with exon 20 insertions (ex20ins) and other uncommon epidermal growth factor receptor (EGFR) mutations", Poster(TPS8670), ASCO 2024.
Nishio et al., "REZILIENT3: Phase 3 study of zipalertinib plus chemotherapy in patients with previously untreated, advanced nonsquamous non-small cell lung cancer (NSCLC) harboring epidermal growth factor receptor (EGFR) exon 20 insertions (ex20ins) mutations", abstract(TPS219), ASCO Breakthrough 2024.
Nishio et al., "REZILIENT3: Phase 3 study of zipalertinib plus chemotherapy in patients with previously untreated, advanced nonsquamous non-small cell lung cancer (NSCLC) harboring epidermal growth factor receptor (EGFR) exon 20 insertions (ex20ins) mutations", Poster(TPS219), ASCO Breakthrough 2024.
Nishio et al., "REZILIENT3: Phase 3 study of zipalertinib plus chemotherapy in patients with previously untreated, advanced nonsquamous non-small cell lung cancer (NSCLC) harboring epidermal growth factor receptor (EGFR) exon 20 insertions (ex20ins) mutations", slides(TPS219), ASCO Breakthrough 2024.
Kurata, et al., "Phase 3 study of zipalertinib plus first-line (1L) platinumbased chemotherapy in patients (pts) with non-small cell lung cancer (NSCLC) harboring EGFR exon 20 insertion (ex20ins) mutations (REZILIENT3): Safety lead-in results", Poster(670P), ESMO Asia 2024.
Kurata, et al., "Phase 3 study of zipalertinib plus first-line (1L) platinumbased chemotherapy in patients (pts) with non-small cell lung cancer (NSCLC) harboring EGFR exon 20 insertion (ex20ins) mutations (REZILIENT3): Safety lead-in results", abstract(670P), Annals of Oncology, vol. 35, Issue S4, 2024, p. S1655.
Passaro et al., "Safety and Antitumor Activity of Zipalertinib in NSCLC Patients (pts) with EGFR Exon 20 Insertion (ex20ins) Mutations Who Received Prior Amivantamab", Abstract(1254MO), Annals of Oncology, vol. 35, Supplement 2, 2024, pp. S803-S804.
Passaro et al., "Safety and Antitumor Activity of Zipalertinib in NSCLC Patients (pts) with EGFR Exon 20 Insertion (ex20ins) Mutations Who Received Prior Amivantamab", slides(1254MO), ESMO congress 2024.
Heymach et al., "REZILIENT3: Randomized phase Ill study of first-line zipalertinib in patients with EGFR exon 20 insertion-mutated NSCLC", Future Oncology, 2025, vol. 21, No. 5, pp. 549-556, https://doi.org/10.1080/14796694.2025.2457294_ Published online: Feb. 16, 2025.
"Cullinan Therapeutics, Taiho Pharmaceutical, and Taiho Oncology to Present Positive Results from Pivotal Phase 2b REZILIENT1 Trial of Zipalertinib at ASCO 2025", news release, 2025.
"Zipalertinib Trial at Columbia University" inspire; Support group for patients with EGFR Exo, 2024 (2 pages) obtained at https://www.inspire.com/groups/exon-20/discussion/zipalertinib-trial-at-columbia-university/.
Gazdar et al., "Inhibition of EGFR Signaling: All Mutations Are Not Created Equal", 2005, PLoS Med, 2(11), 377, https://doi.org/10.137/journal.pmed.0020377.
Piotrowska et al., "1345P—Preliminary safety and activity of CLN-081 in NSCLC with EGFR exon 20 insertion mutations (Ins20)", ESMO Virtual Congress Poster, Annals of Oncology, 2020, 3 pages.
"Cullinan Oncology Announces Updated Phase 1/2a Data for CLN-081 in NSCLC EGFR Exon 20 Patients", Cullinan Oncology, Inc. Press Release, 2021, 3 pages.
"Phase (Ph) 1/2a Study of CLN-081 in NSCLC Patients (pts) with EGFR Exon 20 Insertion Mutations (Ins20)", ASCO 2022 Annual Meeting, Abstract, 2 pages.
Yu et al., "Phase (Ph) 1/2a Study of CLN-081 in NSCLC Patients (pts) with EGFR Exon 20 Insertion Mutations (Ins20)", ASCO 2022 Annual Meeting, Oral Presentation, 14 pages.
Hayashida et al., "Resistance mechanism to CLN-081 (TAS6417), a novel EGFR-TKI, in non-small cell lung cancer (NSCLC) cells with EGFR exon 20 insertions", 2022, AACR2022 Abstract, 2 pages.
CLN-081-001 jRCT Registration Template, 2020, 23 pages (with partial English translation).
Kagawa et al., "Mechanism of CLN-081 resistance in non-small cell lung cancer (NSCLC) with EGFR exon20 insertion mutation (ex20ins)", 2 pages (with unedited computer-generated English translation).
Kagawa et al., "The EGFR C797S Mutation Confers Resistance to a Novel EGFR Inhibitor CLN-081 to EGFR Exon 20 Insertion Mutations", JTO Clinical and Research Reports, 2023, vol. 4, No. 3, 100462, pp. 1-10.
"Cullinan Oncology Announces Clinical and Regulatory Update for CLN-081 in NSCLC EGFR Exon 20 Patients", Cullinan Oncology, Inc. Press Release, 2022, 3 pages.
REZILIENT3 (Researching ZIpaLertinib In Egfr Non-small Cell Lung Cancer Tumors), NCT05973773, Taiho Oncology, Inc., 2023, 16 pages.
A Study of Zipalertinib in Patients With Advanced Non-Small Cell Lung Cancer With Epidermal Growth Factor Receptor (EGFR) Exon 20 Insertions or Other Uncommon Mutation (REZILIENT2), NCT05967689, Taiho Oncology, Inc., 2023, 14 pages.
A Phase 1/2 Trial of CLN-081 in Patients with Non-Small Cell Lung Cancer (REZILIENT1), NCT04036682, Cullinan Therapeutics Inc., 2023, 16 pages.
"Announcement of the Initiation of a Phase III Study of zipalertinib for the Primary Treatment of Non-Small Cell Lung Cancer", Taiho Press Release, 2023, 8 pages (with unedited computer-generated English translation).
REZILIENT3 Global First-Line Trial of Zipalertinib Launched in Patients With Non-Small Cell Lung Cancer Harboring EGFR Exon 20 Insertion Mutations, Taiho Oncology and Cullinan Oncology Initiate Global Phase 3 Clinical Trial Evaluating Zipalertinib in First Line Non-Small Cell Lung Cancer, TOI Press Release, 2023, 6 pages.
Huang, Jinhong, "A Phase 1/2 Open-Label, Multi-Center Trial to Assess Safety, Tolerability Pharmacokinetics, Pharmacodynamics, and Efficacy of CLN-081 in Patients with Locally-Advanced or Metastatic Non-Small Cell Lung Cancer Harboring EGFR Exon 20 Insertion Mutations Who Have Previously Received Platinum-Based Systemic Chemotherapy", jRCT2041230017, Taiho Pharmaceutical Co., Ltd., 2023, 4 pages.
Yu et al., "REZILIENT2: Phase 2 Study of Zipalertinib in Patients With Advanced NSCLC With Exon 20 Insertions and Other Uncommon EGFR Mutations", The IASLC North America Conference on Lung Cancer (NACLC) 2023, Poster and Abstract, 6 pages.
Yu et al., "REZILIENT3: Phase 3 Study of Zipalertinib Plus Chemotherapy in Previously Untreated, Advanced, Nonsquamous NSCLC Patients With EGFR Exon 20 Insertions", The IASLC North America Conference on Lung Cancer (NACLC) 2023, Poster and Abstract, 6 pages.
Yu et al., "REZILIENT2: Phase 2 study of zipalertinib in patients with advanced non-small cell lung cancer (NSCLC) with exon 20 insertions (ex20ins) and other uncommon epidermal growth factor receptor (EGFR) mutations", American Society of Clinical Oncology Annual Meeting (ASCO), 2024, Poster and Abstract, 2 pages.
Yu et al., "REZILIENT3: Phase 3 study of zipalertinib plus chemotherapy in patients with previously untreated, advanced nonsquamous non-small cell lung cancer (NSCLC) harboring epidermal growth

(56) References Cited

OTHER PUBLICATIONS factor receptor (EGFR) exon 20 insertions (ex20ins) mutations", American Society of Clinical Oncology Annual Meeting (ASCO), 2024, Poster and Abstract, 2 pages.

"CLN-619 and Zipalertinib Updated at ASCO", Safety and Antitumor Activity of Zipalertinib in NSCLC Patients with EGFR Exon 20 Insertion (ex20ins) Mutations Who Received Prior Amivantamab, American Society of Clinical Oncology Annual Meeting (ASCO), 2024, Presentation, 35 pages.

Ercan et al., EGFR mutations and resistance to irreversible pyrimidine based EGFR inhibitors, *Clin. Cancer Res.*, 2015; 21:3913-3923, with supplemental materials (25 pages).

Shinji Kohsaka, et al., Supplementary Materials for A method of high-throughput functional evaluation of EGFR gene variants of unknown significance in cancer, Published Nov. 15, 2017, *Sci. Transl. Med.* 9, eaan6566 (2017) (15 pages).

* cited by examiner

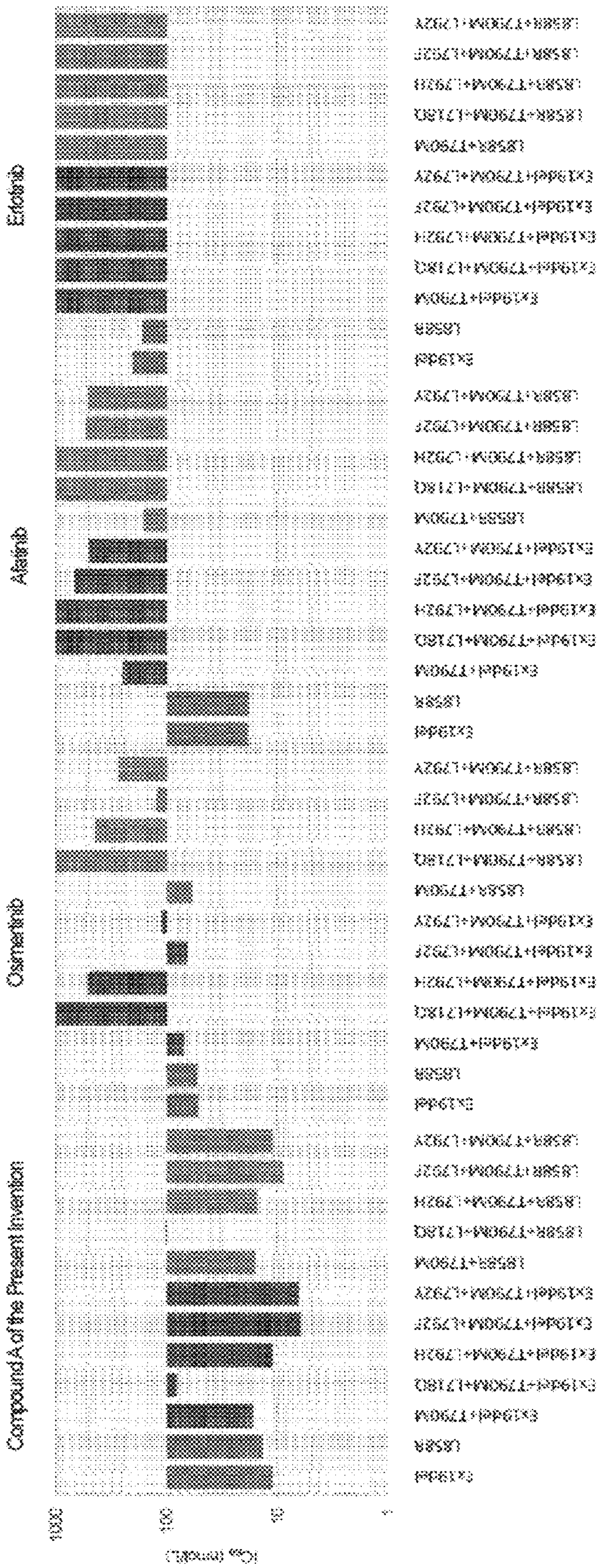
Erlotinib
Afatinib
Osimertinib
Compound A of the Present Invention
1000
100
10

SEQUENCE LISTING

```
<160> NUMBER OF SEQ ID NOS: 1

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

-continued

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
```

-continued

```
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185
```

-continued

```
Gly Ser  Thr Ala Glu Asn Ala  Glu Tyr Leu Arg Val  Ala Pro Gln
    1190                1195                1200

Ser Ser  Glu Phe Ile Gly Ala
    1205                1210
```

1

L718 AND/OR L792 MUTANT TREATMENT-RESISTANT EGFR INHIBITOR

SEQUENCE LISTING

The instant application contains a Sequence Listing which has been submitted via EFS-Web and is hereby incorporated by reference in its entirety. Said ASCII copy, created on Jun. 22, 2021, is named CLN-029WOUS_Sequence_Listing.txt, and is 10,721 bytes in size.

CROSS-REFERENCE TO RELATED APPLICATIONS

This application is the National Stage of International Application No. PCT/JP2019/051377, filed Dec. 27, 2019, published in English under PCT Article 21 (2), which claims the benefit of and priority to JP Patent Application Serial No. 2018-247131, filed on Dec. 28, 2018, the contents of which are incorporated by reference in their entirety.

TECHNICAL FIELD

The present invention relates to an antitumor agent against cancers, comprising an exon 18 and/or exon 20 treatment-resistant mutant epidermal growth factor receptor (hereinafter referred to as "EGFR").

BACKGROUND ART

EGFR is a receptor-type tyrosine kinase, exerts its physiological function in normal tissue by being bound to Epidermal Growth Factor (hereinafter also referred to as EGF), which is a ligand, and contributes to growth and apoptosis inhibition in cp-ithelial tissues (NPL 1). Further, somatic mutation of EGFR gene has been known as a cancer-causing gene; for example, EGFR in which codons 746 to 750 in exon 19 are deleted (hereinafter also referred to as "exon 19 deletion mutation") and EGFR in which leucine encoded by codon 858 in exon 21 is mutated to arginine (hereinafter also referred to as "L858R mutation") constantly induce EGF-independent kinase activity, and contribute to the growth and survival of cancer cells (NPL 2). These mutations are observed, for example, in 30 to 50% of non-small-cell lung cancer in East Asia. The mutations are also observed in about 10% of non-small-cell lung cancer in Europe and the United States, and are regarded as one of the causes of cancers (NPL 3).

Therefore, research and development of EGFR inhibitor as an antitumor agent have actively been conducted, and introduced into the treatment of various EGFR mutation-positive lung cancers (NPL 2 and NPL 4). Gefitinib, erlotinib, and afatinib have been used as therapeutic agents against exon 19 deletion mutant and L858R mutant EGFR-positive lung cancers. Exon 19 deletion mutation and L858R mutation account for 90% of EGFR mutation. Further, occurrence of acquired resistance in the process of the treatment using these agents has been known, and 50% thereof is caused by resistance mutation EGFR in which codon 790 of exon 20 is changed from threonine to methionine (hereinafter also referred to as "T790M mutation"). To treat lung cancers having this mutation, osimertinib has been used as a therapeutic agent. Therefore, treatments using EGFR inhibitors are in the process of being established for lung cancer patients having major EGFR mutations.

CITATION LIST

Patent Literature

PTL 1: WO2015/175632A1
PTL 2: WO2015/025936A1

Non-Patent Literature

NPL 1: Nat. Rev. Cancer, vol. 6, pp. 803-812 (2006)
NPL 2: Nature Medicine, vol. 19, pp. 1389-1400 (2013)
NPL 3: Nat. Rev. Cancer, vol. 7, pp. 169-181 (2007)
NPL 4: Clin. Cancer Res., vol. 24, pp. 3097-3107 (2018)

SUMMARY OF INVENTION

Technical Problem

Treatments using EGFR inhibitors are in the process of being established for lung cancer patients having major EGFR mutations. In contrast, the presence of patients who are resistant to osimertinib treatment has also been known. It is reported that some of the causes thereof are EGFR gene mutations (NPL 4). It has been confirmed that, for example, lung cancer having, in addition to exon 19 deletion mutation or L858R mutation, both of which are de novo mutations, and T790M mutation, which is acquired resistance mutation, point mutation in which leucine encoded by codon 718 in exon 18 is substituted with an arbitrary amino acid (hereinafter also referred to as "L718X mutation") or point mutation in which leucine encoded by codon 792 in exon 20 is substituted with an arbitrary amino acid (hereinafter also referred to as "L792X mutation"), is resistant to osimertinib treatment. It is proposed that amino acid substitution caused by L718X mutation or L792X mutation induces steric hindrance and decrease in hydrophobic binding, thereby preventing EGFR binding to osimertinib (NPL 4). Accordingly, there is a demand for the development of inhibitors having high inhibitory activity against EGFR having composite mutation of de novo active mutation, T790M acquired resistance mutation, and L718X mutation or L792X mutation.

Therefore, the development of drugs having high inhibitory activity against EGFR having composite mutation containing L718X or L792X is assumed to make it possible to exhibit antitumor effects against lung cancer that is resistant to osimertinib treatment, and is expected to contribute to the life prolongation and QOL improvement of mutant EGFR-positive cancer patients for whom no therapy has been established. Further, a drug having high inhibitory activity with respect to T790M, which is acquired resistance mutation against treatments using EGFR inhibitors, is expected to reduce expression frequency of acquired resistance during the treatments using EGFR inhibitors against exon 19 or exon 21 mutant EGFR, which is de novo mutation; and is therefore expected to contribute to the life prolongation of cancer patients.

Under such circumstances, an object of the present invention is to provide an inhibitor that has high inhibitory activity against L718 and L792 mutant EGFR, which is an osimertinib treatment-resistant mutation, and for which the therapeutic effects of the previously known EGFR inhibitors are insufficient.

Solution to Problem

The inventors of the present invention conducted extensive research, and found that EGFR inhibitors conventionally introduced into treatment have poor inhibitory activity against composite mutant EGFR containing L718 and L792 mutations, in addition to active mutation and T790M acquired resistance mutation. Further, the inventors conducted extensive research starting from comparison of the cocrystal structures of compounds, and also found that the compound of the present invention exhibits excellent inhibitory activity against EGFR having L718 and L792 mutations, and further exhibits excellent inhibitory activity against the above composite mutant EGFR. With this finding, the inventors have accomplished the present invention.

The present invention encompasses the following embodiments.

Item 1.

An antitumor agent for treating a malignant tumor patient expressing EGFR having at least one mutation selected from the group consisting of L718X mutation in exon 18 and L792X mutation in exon 20, wherein X represents an arbitrary amino-acid residue, the antitumor agent comprising (S)—N-(4-amino-6-methyl-5-(quinolin-3-yl)-8,9-dihydropyrimido[5,4-b]indolizin-8-yl) acrylamide (Compound (A)) or a salt thereof.

Item 2.

The antitumor agent according to Item 1, wherein the EGFR further has at least one mutation selected from the group consisting of exon 19 deletion mutation, L858R, L861Q, G719X, E709X, and exon 20 insertion mutation.

Item 3.

The antitumor agent according to Item 2, wherein the EGFR further has T790M mutation.

Item 4.

The antitumor agent according to any one of Items 1 to 3, wherein the L718X mutation is L718Q mutation.

Item 5.

The antitumor agent according to any one of Items 1 to 4, wherein the L792X mutation is L792H, L792F, or L792Y.

Item 6.

A method for treating a malignant tumor patient, comprising the step of admin-istering (S)—N-(4-amino-6-methyl-5-(quinolin-3-yl)-8,9-dihydropyrimido[5,4-b]indolizin-8-yl) acrylamide or a salt thereof to a malignant tumor patient expressing EGFR having at least one mutation selected from the group consisting of L718X mutation in exon 18 and L792X mutation in exon 20.

Item 7. (S)—N-(4-amino-6-methyl-5-(quinolin-3-yl)-8,9-dihydropyrimido[5,4-b]indolizin-8-yl) acrylamide or a salt thereof for treating a malignant tumor patient expressing EGFR having at least one mutation selected from the group consisting of L718X mutation in exon 18 and L792X mutation in exon 20.

Item 8.

Use Of (S)—N-(4-amino-6-methyl-5-(quinolin-3-yl)-8,9-dihydropyrimido[5,4-b]indolizin-8-yl) acrylamide or a salt thereof for treating a malignant tumor patient expressing EGFR having at least one mutation selected from the group consisting of L718X mutation in exon 18 and L792X mutation in exon 20.

Item 9.

Use Of (S)—N-(4-amino-6-methyl-5-(quinolin-3-yl)-8,9-dihydropyrimido[5,4-b]indolizin-8-yl) acrylamide or a salt thereof for the production of a pharmaceutical agent for treating a malignant tumor patient expressing EGFR having at least one mutation selected from the group consisting of L718X mutation in exon 18 and L792X mutation in exon 20.

Item 10.

A pharmaceutical composition comprising (S)—N-(4-amino-6-methyl-5-(quinolin-3-yl)-8,9-dihydropyrimido[5,4-b]indolizin-8-yl) acrylamide or a salt thereof and a pharmaceutically acceptable carrier, for treating a malignant tumor patient expressing EGFR having at least one mutation selected from the group consisting of L718X mutation in exon 18 and L792X mutation in exon 20, wherein X represents an arbitrary amino-acid residue.

Item 11.

A method for predicting therapeutic effects of chemotherapy using an antitumor agent comprising, as an active ingredient, (S)—N-(4-amino-6-methyl-5-(quinolin-3-yl)-8,9-dihydropyrimido[5,4-b]indolizin-8-yl) acrylamide or a salt thereof in a malignant tumor patient, the method comprising steps (1) and (2) below:

(1) a step of detecting the presence or absence of mutation of EGFR gene contained in a biological sample obtained from the patient; and (2) a step of predicting that the chemotherapy is highly likely to exhibit sufficient therapeutic effects with respect to the patient when the results of the detection in step (1) find that the EGFR gene has at least one mutation selected from the group consisting of L718X mutation in exon 18 and L792X mutation in exon 20, wherein X represents an arbitrary amino-acid residue.

Item 12.

A method for treating a malignant tumor patient, comprising steps (1) to (3) below:

(1) a step of detecting the presence or absence of mutation of EGFR gene contained in a biological sample obtained from the patient;

(2) a step of predicting that chemotherapy using an antitumor agent comprising, as an active ingredient, (S)—N-(4-amino-6-methyl-5-(quinolin-3-yl)-8,9-dihydropyrimido[5,4-b]indolizin-8-yl) acrylamide or a salt thereof is highly likely to exhibit sufficient therapeutic effects with respect to the patient when the results of the detection in step (1) find that the EGFR gene has at least one mutation selected from the group consisting of L718X mutation in exon 18 and L792X mutation in exon 20, wherein X represents an arbitrary amino-acid residue; and (3) a step of administering (S)—N-(4-amino-6-methyl-5-(quinolin-3-yl)-8,9-dihydropyrimido[5,4-b]indolizin-8-yl) acrylamide or a salt thereof to a malignant tumor patient who has been predicted highly likely to sufficiently respond to the chemotherapy using an antitumor agent comprising, as an active ingredient, (S)—N-(4-amino-6-methyl-5-(quinolin-3-yl)-8,9-dihydropyrimido[5,4-b]indolizin-8-yl) acrylamide or a salt thereof, in step (2).

Advantageous Effects of Invention

The antitumor agent of the present invention exerts high inhibitory activity against EGFR having L718 and L792 mutations. Therefore, the antitumor agent of the present invention is useful in view of providing an antitumor agent that exerts superior therapeutic effects for a malignant tumor patient expressing EGFR having L718 and L792 mutations.

The present invention is also useful in terms of providing a method for treating a malignant tumor patient expressing EGFR having L718 and L792 mutations.

The EGFR inhibitory activity of conventional EGFR inhibitors was remarkably reduced under the presence of T790M mutation, which is acquired resistance mutation in the exon 20 region, or under the presence of L718 and L792 mutations. Thus, it was difficult to exert sufficient therapeutic effects. In contrast, the antitumor agent of the present invention has high inhibitory activity against EGFR having L718 and/or L792 mutation, as well as having active mutation, such as Ex 19del or L858R mutation; thus, the antitumor agent of the present invention can exert superior therapeutic effects for a malignant tumor patient expressing EGFR having these complex mutations. The antitumor agent of the present invention has high inhibitory activity against EGFR having L718 and/or L792 mutation, even though it has T790M mutation in addition to the above mutations; thus, the antitumor agent of the present invention can exert superior therapeutic effects for a malignant tumor patient expressing EGFR complexly having these mutations.

Further, the antitumor agent of the present invention is also useful in terms of reducing expression frequency of acquired resistance during the treatments using EGFR inhibitors against exon 18 or exon 21 mutant EGFR, which is de novo mutation, because of its high inhibitory activity against exon 18 and exon 20 treatment-resistant mutant EGFR even under the presence of T790M mutation, which is acquired resistance mutation in the exon 20 region.

BRIEF DESCRIPTION OF DRAWINGS

FIG. 1 illustrates the evaluation results of phosphorylation (inhibitory activity) in a mutant EGFR forced expression system using HEK293 cells.

DESCRIPTION OF EMBODIMENTS

Preferable examples of various definitions in the scope of the present invention used in this specification are explained below in detail.

In this specification, "EGFR" refers to a human epidermal growth factor receptor protein, and is also referred to as ErbB-1 or HER1.

In this specification, "wild-type EGFR" refers to EGFR free of somatic mutation, which is a protein comprising the amino acid sequence represented by SEQ ID NO: 1 (GenBank accession number: NP_005219.2).

In this specification, "exon 18" refers to 688-728 region in the amino acid sequence of wild-type EGFR (SEQ ID NO: 1).

In this specification, "exon 18 treatment-resistant mutation" refers to point mutation or deletion mutation in amino acid in the exon 18 region of wild-type EGFR (SEQ ID NO: 1). Preferable exon 18 treatment-resistant mutation is point mutation with 1 amino acid substitution in the exon 18 region. More preferably, the exon 18 treatment-resistant mutation is L718X (X represents, among amino acids constituting a protein encoded by genetic information, an arbitrary amino-acid residue other than leucine), which is point mutation in which leucine encoded by codon 718 of exon 18 is substituted with an arbitrary amino acid. More specifically, preferable examples of L718X include L718Q, which is point mutation in which leucine encoded by codon 718 in the exon 18 region is substituted with glutamine; and L718V, which is point mutation in which leucine encoded by codon 718 is substituted with valine.

In this specification, "exon 18 active mutation" refers to point mutation or deletion mutation in amino acid in the exon 18 region of wild-type EGFR (SEQ ID NO: 1). Preferable exon 18 active mutation is point mutation with 1 amino acid substitution in the exon 18 region. More preferably, the exon 18 active mutation is E709X, which is point mutation in which glutamic acid encoded by codon 709 of exon 18 is substituted with an arbitrary amino acid; or G719X, which is point mutation in which glycine encoded by codon 719 of exon 18 is substituted with an arbitrary amino acid. More specifically, preferable examples of E709X include E709K, which is point mutation in which glutamic acid encoded by codon 709 in the exon 18 region is substituted with lysine; and E709A, which is point mutation in which glutamic acid encoded by codon 709 in the exon 18 region is substituted with alanine. Preferable examples of G719X include G719A, which is point mutation in which glycine encoded by codon 719 in the exon 18 region is substituted with alanine; G719S, which is point mutation in which glycine encoded by codon 719 in the exon 18 region is substituted with serine; and G719C, which is point mutation in which glycine encoded by codon 719 in the exon 18 region is substituted with cysteinc.

In the present invention, "exon 20" refers to 824-875 region in the amino acid sequence of wild-type EGFR (SEQ ID NO: 1).

In this specification, "exon 20 treatment-resistant mutation" refers to point mutation in amino acid in the exon 20 region of wild-type EGFR (SEQ ID NO: 1). Preferable exon 20 treatment-resistant mutation is point mutation with 1 amino acid substitution in the exon 20 region. More preferably, the exon 20 treatment-resistant mutation is L792X (X represents, among amino acids constituting a protein encoded by genetic information, an arbitrary amino-acid residue other than leucine), which is point mutation in which leucine encoded by codon 792 in the exon 20 region is substituted with an arbitrary amino acid. Specific examples include L792H, which is point mutation in which leucine encoded by codon 792 in the exon 20 region is substituted with histidine; L792F, which is point mutation in which leucine encoded by codon 792 is substituted with phenylalanine; L792Y, which is point mutation in which leucine encoded by codon 792 is substituted with tyrosine; L792R, which is point mutation in which leucine encoded by codon 792 is substituted with arginine; L792V, which is point mutation in which leucine encoded by codon 792 is substituted with valine; and L792P, which is point mutation in which leucine encoded by codon 792 is substituted with proline. Among these, L792F, L792H, and L792Y are preferable.

In this specification, "exon 20 insertion mutation" refers to mutation with insertion of one or more (preferably 1 to 7, more preferably 1 to 4) amino acids into the exon 20 region of EGFR (761 to 823 amino acid sequence in SEQ ID NO: 1). Preferable examples include mutation with insertion of amino acid sequence FQEA (phenylalanine, glutamine, glutamic acid, and alanine sequentially from the N-terminal side) between 763 alanine and 764 tyrosine in the exon 20 region (A763_Y764insFQEA), mutation with insertion of amino acid sequence ASV (alanine, serine, and valine sequentially from the N-terminal side) between 769 valine and 770 asparagic acid in the exon 20 region (V769_D770insASV), mutation with insertion of amino acid sequence SVD (serine, valine, and asparagic acid sequentially from the N-terminal side) between 770 asparagic acid and 771 asparagine in the exon 20 region (D770_N771insSVD), mutation with insertion of amino acid sequence NPG (asparagine, proline, and glycine sequentially from the N-terminal side) between 770 asparagic acid and 771 asparagine in the exon 20 region (D770_N771insNPG), mutation with insertion of amino acid G (glycine) between 770 asparagic acid and 771 asparagine in the exon 20 region (D770_N771insG), mutation with insertion of amino acid sequence GY (glycine and tyrosine sequentially from the N-terminal side) after deletion of 770 asparagic acid in the exon 20 region (D770>GY), mutation with insertion of amino acid N (asparagine) between 771 asparagine and 772 proline in the exon 20 region (N771_P772insN), mutation with insertion of amino acid sequence PR (proline and arginine sequentially from the N-terminal side) between 772 proline and 773 histidine in the exon 20 region (P772_R773insPR), mutation with insertion of amino acid sequence NPH (asparagine, proline, and histidine sequentially from the N-terminal side) between 773 histidine and 774 valine in the exon 20 region (H773_V774insNPH), mutation with insertion of amino acid sequence PH (proline and histidine sequentially from the N-terminal side) between 773 histidine and 774 valine in the exon 20 region (H773_V774insPH), mutation with insertion of amino acid sequence AH (alanine and histidine sequentially from the N-terminal side) between 773 histidine and 774 valine in the exon 20 region (H773_V774insAH), mutation with insertion of amino acid H (histidine) between 773 histidine and 774 valine in the exon 20 region (H773_V774insH), mutation with insertion of amino acid sequence HV (histidine and valine sequentially from the N-terminal side) between 774 valine and 775 cysteine in the exon 20 region (V774_C774insHV), mutation with insertion of amino acid sequence EAFQ (glutamic acid, alanine, phenylalanine, and glutamine sc-quentially from the N-terminal side) between 761 alanine and 762 glutamic acid in the exon 20 region (A761_E762insEAFQ), and the like. More preferable examples include mutation with insertion of amino acid sequence ASV (alanine, serine, and valine sequentially from the N-terminal side) between 769 valine and 770 asparagic acid in the exon 20 region (V769_D770insASV), mutation with insertion of amino acid sequence SVD (serine, valine, and asparagic acid sequentially from the N-terminal side) between 770 asparagic acid and 771 asparagine in the exon 20 region (D770_N771insSVD), mutation with insertion of amino acid G (glycine) between 770 asparagic acid and 771 asparagine in the exon 20 region (D770_N771insG), mutation with insertion of amino acid sequence NPH (asparagine, proline, and histidine sequentially from the N-terminal side) between 773 histidine and 774 valine in the exon 20 region (H773_V774insNPH), and mutation with insertion of amino acid sequence PH (proline and histidine sequentially from the N-terminal side) between 773 histidine and 774 valine in the exon 20 region (H773_V774insPH). Particularly preferable examples include mutation with insertion of amino acid sequence FQEA (phenylalanine, glutamine, glutamic acid, and alanine sequentially from the N-terminal side) between 763 alanine and 764 tyrosine in the exon 20 region (A763_Y764insFQEA), mutation with insertion of amino acid sequence ASV (alanine, serine, and valine sequentially from the N-terminal side) between 769 valine and 770 asparagic acid in the exon 20 region (V769_D770insASV), mutation with insertion of amino acid sequence SVD (serine, valine, and asparagic acid sequentially from the N-terminal side) between 770 asparagic acid and 771 asparagine in the exon 20 region (D770_N771insSVD), mutation with insertion of amino acid G (glycine) between 770 asparagic acid and 771 asparagine in the exon 20 region (D770_N771insG), mutation with insertion of amino acid sequence NPH (asparagine, proline, and histidine sequentially from the N-terminal side) between 773 histidine and 774 valine in the exon 20 region (H773_V774inchsNPH), mutation with insertion of amino acid sequence PH (proline and histidine sequentially from the N-terminal side) between 773 histidine and 774 valine in the exon 20 region (H773_V774insPH), and the like.

In the present invention, “exon 21” refers to 824-875 region in the amino acid sequence of wild-type EGFR (SEQ ID NO: 1).

In this specification, “exon 21 active mutation” refers to point mutation in amino acid in the exon 21 region of wild-type EGFR (SEQ ID NO: 1). Preferable exon 21 active mutation is point mutation with 1 amino acid substitution in the exon 21 region. More preferably, the exon 21 active mutation is L858X, which is point mutation in which leucine encoded by codon 858 in the exon 21 region is substituted with an arbitrary amino acid; or L861X, which is point mutation in which leucine encoded by codon 861 in the exon 21 region is substituted with an arbitrary amino acid (X represents, among amino acids constituting a protein encoded by genetic information, an arbitrary amino-acid residue other than leucine). More specifically, preferable examples include L858R, which is point mutation in which leucine encoded by codon 858 in the exon 21 region is mutated to arginine; and L861Q, which is point mutation in which leucine encoded by codon 861 in the exon 21 region is substituted with glutamine.

In the present invention, “exon 18 and/or exon 20 treatment-resistant mutation” encompasses “exon 18 treatment-resistant mutation,” “exon 20 treatment-resistant mutation,” and “exon 18 and exon 20 treatment-resistant mutation.”

In the present invention, “point mutation” refers to mutation causing substitution, insertion, or deletion of one or more (e.g., about 1 to 10, preferably about 1 to 5, more preferably about 1, 2, or 3) amino-acid residues; and may include in-frame insertion and/or deletion mutation as nucleic acid.

“EGFR having exon 18 and/or exon 20 treatment-resistant mutation” encompasses “EGFR having exon 18 treatment-resistant mutation,” “EGFR having exon 20 treatment-resistant mutation,” and “EGFR having exon 18 and exon 21 treatment-resistant mutation.”

In this specification, “EGFR having exon 18 treatment-resistant mutation” refers to EGFR having at least the above L718X mutation in exon 18 as the exon 18 treatment-resistant mutation. The EGFR may further have an exon 18 mutation other than L718X, but preferably has a single L718X mutation as the exon 18 treatment-resistant mutation. Moreover, the EGFR may have a mutation other than exon 18 treatment-resistant mutation (e.g., exon 19 deletion mutation, L858R mutation, and L790M mutation).

In this specification, the “EGFR having exon 20 treatment-resistant mutation” refers to EGFR having at least the above L792X mutation in exon 20 as the exon 20 treatment-resistant mutation. The EGFR may have a mutation other than L792X mutation, but preferably has a single L718X mutation as the exon treatment-resistant 20 mutation. Moreover, the EGFR may have a mutation other than exon 20 treatment-resistant mutation (e.g., exon 19 deletion mutation, L858R mutation, and L790M mutation).

In this specification, “exon 19” refers to 729-823 region in the amino acid sequence of wild-type EGFR (SEQ ID NO: 1).

In this specification, “exon 19 deletion mutation” refers to mutation with deletion of one or more amino acids in the exon 19 region of wild-type EGFR (SEQ ID NO: 1). In addition to deletion in this region, mutation with insertion of one or more arbitrary amino acids is also included. Examples of exon 19 deletion mutation include mutation with deletion of 5 amino acids from 746 glutamic acid to 750 alanine in the exon 19 region (Del E746-A750), mutation with insertion of serine after deletion of 7 amino acids from 747 leucine to 753 proline in the exon 19 region (Del 747-P753insS), mutation with deletion of 5 amino acids from 747 leucine to 751 threonine in the exon 19 region (Del L747-T751), mutation with insertion of proline after deletion of 4 amino acids from 747 leucine to 750 alanine in the exon 19 region (Del 747-A750insP), and the like. Preferable examples include mutation with deletion of 5 amino acids from 746 glutamic acid to 750 alanine in the exon 19 region (Del E746-A750).

Moreover, the EGFR having exon 18 and/or exon 20 treatment-resistant mutation may further have at least one mutation selected from the group consisting of exon 19 deletion mutation, L858R, L861Q, G719X, E709X, and exon 20 insertion mutation. Specific examples include EGFR having L718X mutation in the exon 18 region further having exon 19 deletion mutation, EGFR having L792X mutation in the exon 20 region further having exon 19 deletion mutation, EGFR having L718X mutation in the exon 18 region further having L858R, EGFR having L792X mutation in the exon 20 region further having L858R, EGFR having L718X mutation in the exon 18 region further having L861Q, EGFR having L792X mutation in the exon 20 region further having L861Q, EGFR having L718X mutation in the exon 18 region further having G719X, EGFR having L792X mutation in the exon 20 region further having G719X, EGFR having L718X mutation in the exon 18 region further having E709X, EGFR having L792X mutation in the exon 20 region further having E709X, EGFR having L718X mutation in the exon 18 region further having exon 20 insertion mutation, and EGFR having L792X mutation in the exon 20 region further having exon 20 insertion mutation. Preferable among these are EGFR having L718X mutation in the exon 18 region further having exon 19 deletion mutation, EGFR having L792X mutation in the exon 20 region further having exon 19 deletion mutation, EGFR having L718X mutation in the exon 18 region further having L858R, and EGFR having L792X mutation in the exon 20 region further having L858R.

Further, the EGFR having exon 18 and/or exon 20 treatment-resistant mutation may further have T790M mutation, in addition to the above exon 19 deletion mutation, L858R, L861Q, G719X, E709X, and exon 20 insertion mutation. T790M is acquired resistance mutation in the exon 20 region. T790M is known to be generated by the use of existing EGFR inhibitors. The acquisition of T790M often decreases the effects of existing drugs with respect to malignant tumor patients.

In the present invention, examples include EGFR having L718X mutation in the exon 18 region having exon 19 deletion mutation further having T790M mutation, EGFR having L792X mutation in the exon 20 region having exon 19 deletion mutation further having T790M mutation, EGFR having L718X mutation in the exon 18 region having L858R further having T790M mutation, EGFR having L792X mutation in the exon 20 region having L858R further having T790M mutation, EGFR having L718X mutation in the exon 18 region having L861Q further having T790M mutation, EGFR having L792X mutation in the exon 20 region having L861Q further having T790M mutation, EGFR having L718X mutation in the exon 18 region having G719X further having T790M mutation, EGFR having L792X mutation in the exon 20 region having G719X further having T790M mutation, EGFR having L718X mutation in the exon 18 region having E709X further having T790M mutation, EGFR having L792X mutation in the exon 20 region having E709X further having T790M mutation, EGFR having L718X mutation in the exon 18 region having exon 20 insertion mutation further having T790M mutation, and EGFR having L792X mutation in the exon 20 region having exon 20 insertion mutation further having T790M mutation. Preferable among these are EGFR having L718X mutation in the exon 18 region having exon 19 deletion mutation further having T790M mutation, EGFR having L792X mutation in the exon 20 region having exon 19 deletion mutation further having T790M mutation, EGFR having L718X mutation in the exon 18 region having L858R further having T790M mutation, and EGFR having L792X mutation in the exon 20 region having L858R further having T790M mutation.

Among the EGFRs having the above composite mutations, EGFR having L718Q mutation in the exon 18 region, EGFR having L792F mutation in the exon 20 region, EGFR having L792H mutation, and EGFR having L792Y mutation are particularly preferable.

In the present invention, the method for detecting mutations in EGFR expressed by a malignant tumor patient is not particularly limited insofar as the method is capable of detecting the mutations, and any known detection methods may be used.

The sample used in the detection of EGFR mutation is not particularly limited as long as the sample is a biological sample isolated from a malignant tumor patient, in particular, a sample obtained from a malignant tumor patient and containing malignant tumor cells. Examples of biological samples include body fluids (e.g., blood, urine, etc.), tissues, the extracts thereof, and the cultures of obtained tissues. The method for obtaining a biological sample can be suitably selected depending on the type of biological sample.

The biological sample is prepared by being appropriately treated according to the measurement method. Further, the reagent comprising a primer or probe used for the detection may be prepared by a conventional method according to the measurement method therefor.

In one embodiment of the present invention, a step of detecting the presence of the mutation of the present invention in EGFR expressed by a malignant tumor patient may be performed before the administration of an antitumor agent to the malignant tumor patient.

A malignant tumor may include two or more different kinds of malignant tumor cells. Further, two or more malignant tumors may be generated in a single patient. Therefore, a single patient may have different mutations of EGFR (for example, the exon 18 mutation is L718Q and L718V exon 18 mutation; and the exon 20 mutation is L792F, L792H, L792Y, L792R, L792V, and L792P exon 20 mutation; however, there is no limitation thereto) at the same time.

The antitumor agent of the present invention comprises, as an active ingredient, (S)—N-(4-amino-6-methyl-5-(quinolin-3-yl)-8,9-dihydropyrimido[5,4-b]indolizin-8-yl) acrylamide (Compound (A)) or a salt thereof. Compound (A) is represented by the following chemical formula.

[Chem. 1]

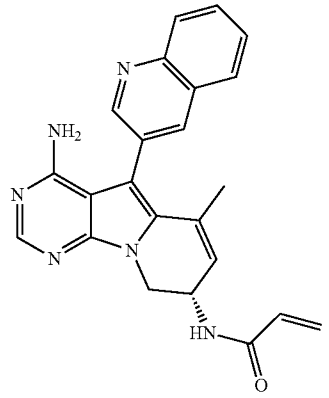

The method for producing the compound of the present invention is explained below. Compound A of the present invention may be produced, for example, through the production method disclosed in WO2015/025936A1, the methods described in the Examples, and the like. However, the production method of the compound of the present invention is not limited to these reaction examples.

When Compound A of the present invention has isomers such as optical isomers, stereoisomers, and tautomers, any of the isomers and mixtures thereof are included within the scope of the compound of the present invention, unless otherwise specified. For example, when the compound of the present invention has optical isomers, racemic mixtures and the optical isomers separated from a racemic mixture are also included within the scope of the compound of the present invention, unless otherwise specified.

The salts of Compound A refer to any pharmaceutically acceptable salts; examples include base addition salts and acid addition salts.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, tri-ethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates.

The compound of the present invention or salts thereof also encompass prodrugs thereof. A prodrug refers to a compound that can be converted to the compound of the present invention or a salt thereof through a reaction with an enzyme, gastric acid, or the like, under physiological conditions in vivo, i.e., a compound that can be converted to the compound of the present invention or a salt thereof by enzymatic oxidation, reduction, hydrolysis, or the like; or a compound that can be converted to the compound of the present invention or a salt thereof by hydrolysis or the like with gastric acid or the like. Further, the prodrug may be a compound that can be converted to the compound of the present invention or a salt thereof under physiological conditions, such as those described in "Iyakuhin no Kaihatsu [Development of Phar-maceuticals]," Vol. 7, Molecular Design, published in 1990 by Hirokawa Shoten Co., pp. 163-198.

Description of Diseases

Specific examples of tumors targeted in the present invention include, but are not particularly limited to, head and neck cancer, gastrointestinal cancer (esophageal cancer, stomach cancer, duodenal cancer, liver cancer, biliary cancer (e.g., gallbladder and bile duct cancer), pancreatic cancer, colorectal cancer (e.g., colon cancer and rectal cancer), etc.), lung cancer (e.g., non-small-cell lung cancer, small-cell lung cancer, and mesothelioma), breast cancer, genital cancer (ovarian cancer, uterine cancer (e.g., cervical cancer and endometrial cancer), etc.), urological cancer (e.g., kidney cancer, bladder cancer, prostate cancer, and testicular tumor), hematopoietic tumor (e.g., leukemia, malignant lymphoma, and multiple myeloma), osteosarcoma, soft-tissue sarcoma, skin cancer, brain tumor, and the like. Preferable examples include lung cancer, breast cancer, head and neck cancer, brain tumor, uterine cancer, gastrointestinal cancer, hematopoietic tumor, and skin cancer. Lung cancer is particularly preferable.

When the compound of the present invention or a salt thereof is used as a pharmaceutical agent, a pharmaceutical carrier can be added, if required, thereby forming a suitable dosage form according to prevention and treatment purposes. Examples of the dosage form include oral preparations, injections, suppositories, ointments, patches, and the like. Oral preparations are preferable. Such dosage forms can be formed by methods conventionally known to persons skilled in the art.

As the pharmaceutically acceptable carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations are prepared as follows. After an excipient is added optionally with an excipient, binder, disintegrant, lubricant, colorant, taste-masking or flavoring agent, etc., to the compound of the present invention, the resulting mixture is formulated into tablets, coated tablets, granules, powders, capsules, or the like by ordinary methods.

Examples of excipients include lactose, sucrose, D-mannitol, glucose, starch, calcium carbonate, kaolin, microcrystalline cellulose, and silicic acid anhydride. Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like. Examples of disintegrators include dry starch, sodium alginate, powdered agar, sodium hydrogen carbonate, calcium carbonate, sodium lauryl sulfate, stearic acid monoglyceride, lactose, and the like. Examples of lubricants include purified talc, sodium stearate, magnesium stearate, borax, polyethylene glycol, and the like. Examples of colorants include titanium oxide, iron oxide, and the like. Examples of taste-masking or flavoring agents include sucrose, bitter orange peel, citric acid, tartaric acid, and the like.

When a liquid preparation for oral administration is prepared, a taste-masking agent, a buffer, a stabilizer, a flavoring agent, and the like may be added to the compound of the present invention; and the resulting mixture may be formulated into an oral liquid preparation, syrup, elixir, etc., according to an ordinary method.

When an injection agent is prepared, a pH regulator, a buffer, a stabilizer, an isotonizing agent, a local anesthetic, and the like, may be added to the compound of the present invention; and the mixture may be formulated into a subcutaneous, intra-muscular, or intravenous injection according to an ordinary method.

Examples of the pH adjuster and the buffer used herein include sodium citrate, sodium acetate, and sodium phosphate. Examples of the stabilizer include sodium py-rosulfite, EDTA, thioglycolic acid, and thiolactic acid. Examples of the local anesthetic include procaine hydrochloride and lidocaine hydrochloride. Examples of the isotonizing agent include sodium chloride, glucose, D-mannitol, and glycerol.

When a suppository is prepared, pharmaceutically acceptable carriers known in the related field, such as polyethylene glycol, lanolin, cacao butter, and fatty acid triglyceride; and, as necessary, surfactants such as Tween 80 (registered trademark), may be added to Compound A, and the resulting mixture may be formulated into a suppository according to an ordinary method.

When an ointment is prepared, a commonly used base, stabilizer, wetting agent, preservative, and the like, may be blended into Compound A, as necessary; and the obtained mixture is mixed and formulated into an ointment according to an ordinary method.

Examples of the base include liquid paraffin, white petrolatum, white beeswax, octyl dodecyl alcohol, and paraffin.

Examples of the preservative include methyl paraoxybenzoate, ethyl paraoxybenzoate, and propyl paraoxybenzoate.

When a patch is prepared, the above-described ointment, cream, gel, paste, or the like, may be applied to an ordinary substrate according to an ordinary method.

Examples of substrates include woven fabrics or non-woven fabrics comprising cotton, staple fibers, or chemical fibers; and films or foam sheets of soft vinyl chloride, polyethylene, polyurethane, etc., may also be used.

The amount of Compound A to be incorporated in each of such dosage unit forms depends on the condition of the patient to whom the compound is administered, the dosage form thereof, etc. In general, in the case of an oral agent, the amount of the compound is preferably 0.05 to 1000 mg per dosage unit form. In the case of an injection, the amount of the compound is preferably 0.01 to 500 mg per dosage unit form; and in the case of a suppository, the amount of the compound is preferably 1 to 1000 mg per dosage unit form.

Further, the daily dose of the medicine in such a dosage form depends on the condition, body weight, age, sex, etc., of the patient, and cannot be generalized. Usually, the daily dose for an adult (body weight: 50 kg) of the compound of the present invention may generally be 0.05 to 5000 mg, and preferably 0.1 to 1000 mg; and is preferably administered in one dose, or in two to three divided doses, per day.

The present invention also provides a method for treating a malignant tumor patient, comprising the step of administering Compound A or a salt thereof to a malignant tumor patient expressing EGFR having exon 18 and/or exon 20 treatment-resistant mutation.

The present invention also provides Compound A or a salt thereof for treating a malignant tumor patient expressing EGFR having exon 18 and/or exon 20 treatment-resistant mutation.

The present invention also provides use of Compound A or a salt thereof for treating a malignant tumor patient expressing EGFR having exon 18 and/or exon 20 treatment-resistant mutation.

The present invention also provides use of Compound A or a salt thereof for the production of a pharmaceutical agent for treating a malignant tumor patient expressing EGFR having exon 18 and/or exon 20 treatment-resistant mutation.

The present invention also provides a method for predicting therapeutic effects of chemotherapy using an antitumor agent comprising, as an active ingredient, Compound A or a salt thereof in a malignant tumor patient, the method comprising steps (1) and (2) below:

(1) a step of detecting the presence or absence of mutation of EGFR gene contained in a biological sample obtained from the patient; and (2) a step of predicting that the chemotherapy is highly likely to exhibit sufficient therapeutic effects to the patient when the results of the detection in step (1) find that the EGFR gene has exon 18 and/or exon 20 treatment-resistant mutation.

The present invention also provides a method for treating a malignant tumor patient, comprising steps (1) to (3) below:

(1) a step of detecting the presence or absence of mutation of EGFR gene contained in a biological sample obtained from the patient; and (2) a step of predicting that chemotherapy using an antitumor agent comprising, as an active ingredient, (S)—N-(4-amino-6-methyl-5-(quinolin-3-yl)-8,9-dihydropyrimido[5,4-b]indolizin-8-yl) acrylamide or a salt thereof is highly likely to exhibit sufficient therapeutic effects with respect to the patient when the results of the detection in step (1) find that the EGFR gene has exon 18 and/or exon 20 treatment-resistant mutation; and (3) a step of administering (S)—N-(4-amino-6-methyl-5-(quinolin-3-yl)-8,9-dihydropyrimido[5,4-b]indolizin-8-yl) acrylamide or a salt thereof to a malignant tumor patient who has been predicted highly likely to sufficiently respond to the chemotherapy using an antitumor agent comprising, as an active ingredient, (S)—N-(4-amino-6-methyl-5-(quinolin-3-yl)-8,9-dihydropyrimido[5,4-b]indolizin-8-yl) acrylamide or a salt thereof, in step (2).

The base sequence of EGFR gene is publicly known. The GenBank accession number of the base sequence of cDNA is NM_005228.4.

The "therapeutic effects" can be evaluated by tumor shrinkage effects, relapse-suppressing effects, life-prolonging effects, and the like. The relapse-suppressing effects may be shown as the degree of the extension of non-relapse period or the degree of the improvement in relapse rate; and the life-prolonging effects may be shown as the degree of the entire survival time or the degree of the extension of the median of progression-free survival, or the like. The "sufficient therapeutic effects" of the chemotherapy using an antitumor agent comprising, as an active ingredient, Compound A or a salt thereof means, for example, that superior therapeutic effects are obtained by the administration of the antitumor agent comprising, as an active ingredient, Compound A or a salt thereof, such as extension of survival time, suppression of relapse, and the like, compared with non-administration.

EXAMPLES

The following describes the present invention in more detail with reference to the following Test Example. However, the present invention is not limited to this Example (Test Example).

Test Example 1

In Vitro Drug Efficacy Test

Evaluation Results of Intracellular Phosphorylation in Mutant EGFR Forced ExPression System Using HEK293 Cells (Inhibitory Activity)

The intracellular target inhibitory activity of compounds was evaluated based on the following as an index: intracellular EGFR phosphorylation in a mutant EGFR forced expression system using Jump-In (trademark) Grip (trademark) HEK293 cells (Thermo Fisher Scientific Inc.) (hereinafter also referred to as "HEK293 cells"). The HEK293 cells were maintained in D-MEM with GlutaMAX (trademark)-I (high glucose) (Thermo Fisher Scientific Inc.) that contained 10% dialyzed FBS. The HEK293 cells were seeded in each well of a 96-well flat-bottom microplate such that the cell count per well was 10,000, and incubated in a 5% $CO_2$ gas-containing incubator at 37° C. overnight. Then, a pcDNATM 6.2/V5-DEST vector encoding a human EGFR gene (Del E746-A750 (hereinafter also referred to as "Ex 19del"), Ex 19del+T790M (the symbol "+" indicates that both mutations are contained), Ex 19del+T790M+L718Q, Ex19del+T790M+L792H, Ex19del+T790M+L792F, Ex19del+T790M+L792Y, L858R, L858R+T790M, L858R+T790M+L718Q, L858R+T790M+L792H, L858R+T790M+L792F, or L858R+T790M+L792Y) was introduced, together with Opti-MEM (trademark) I (Thermo Fisher Scientific Inc.), using a ViaFect (trademark) Transfection Reagent (Promega Corporation). The cells were incubated again in a 5% $CO_2$ gas-containing incubator at 37° C. overnight. The following day, Compound A, erlotinib, afatinib, and osimertinib (erlotinib, afatinib, and osimertinib may each be hereinafter referred to as a "comparative compound") were individually dissolved in DMSO, and diluted with DMSO or a medium. The solutions were then individually added to each well of the culture plate of the cells, and the cells were incubated in a 5% $CO_2$ gas-containing incubator at 37° C. for 6 hours. After incubation, the cells were immobilized using 20% neutral buffered formalin (Wako Pure Chemical Industries, Ltd.), and blocked by an Odyssey (trademark) blocking buffer (PBS) (M&S Tech-noSystems Inc.). The cells were then reacted with a primary antibody (EGFR Antibody Cocktail #AHR5062 (Thermo Fisher Scientific Inc.) and a Phospho-EGFR Receptor (Tyr1068) Antibody #2234L (CST)) diluted with an Odyssey (trademark) blocking buffer (PBS) to 1/200, and the cells were allowed to stand at 4° C. overnight. The following day, the cells were reacted with a secondary antibody (IRDye 800CW Goat aRabbit #926-32211 and IRDye 680RD Goat aMouse #926-68070 (M&S Tech-no-Systems Inc.)) diluted with an Odyssey (trademark) blocking buffer (PBS) to 1/800, and the cells were allowed to stand at room temperature for 1 hour. The fluorescence intensity (hereinafter also referred to as "FI") was detected with an Odyssey (trademark) CLx Infrared Imaging System (LI-COR Bioscience) at a fluorescence wavelength of 800 nm and 700 nm.

The value obtained by subtracting the FI of a well without the primary antibody from the FI detected at a fluorescence wavelength of 800 nm or 700 nm was referred to as FI (800, EGFR)-Blank (for 800 nm) and FI (700, p-EGFR)-Blank (for 700 nm). The value obtained by dividing FI (700, p-EGFR)-Blank of each well by FI (800, EGFR)-Blank was determined to be FI (p-EGFR/EGFR). The phosphorylated EGFR rate was calculated using the following formula to determine the concentration of the test compounds at which EGFR was phosphorylated by 50% ($IC_{50}$ (μM)). Table 1 illustrates the results.

$$\text{Phosphorylated EGFR Rate } (\%) = T/C \times 100$$

T: FI (p-EGFR/EGFR) of a well to which a test compound was added.

C: FI (p-EGFR/EGFR) of a well to which a test compound was not added.

As is clear from Table 1, Compound A exhibited high inhibitory activity against intracellular phosphorylation of composite mutant EGFR containing L718Q and L792X; and the activity was higher than that of erlotinib, afatinib, and osimertinib.

TABLE 1

| | Compound A of the present invention | Osimertinib | Afatinib | Erlotinib |
|---|---|---|---|---|
| Ex19del | 11.2 ± 6.4 | 52.1 ± 23.6 | 18.5 ± 10.2 | 201 ± 6 |
| Ex19del + T790M | 16.9 ± 5.9 | 69.7 ± 15.6 | 250 ± 64 | >1000 |
| Ex19del + T790M + L718Q | 82.5 ± 9.0 | 5800 ± 2940 | >10000 | >10000 |
| Ex19del + T790M + L792H | 11.1 ± 5.6 | 513 ± 280 | 8190 ± 560 | >10000 |
| Ex19del + T790M + L792F | 6.25 ± 1.83 | 65.7 ± 15.5 | 692 ± 325 | >10000 |
| Ex19del + T790M + L792Y | 6.54 ± 1.49 | 111 ± 38 | 508 ± 218 | >10000 |
| L858R | 13.8 ± 3.8 | 53.3 ± 11.0 | 17.9 ± 3.0 | 167 ± 22 |
| L858R + T790M | 16.0 ± 2.6 | 59.0 ± 10.9 | 162 ± 38 | >1000 |
| L858R + T790M + L718Q | 104 ± 40 | 7880 ± 950 | 3670 ± 1690 | >10000 |
| L858R + T790M + L792H | 15.3 ± 5.0 | 441 ± 161 | 2190 ± 1310 | >10000 |
| L858R + T790M + L792F | 9.07 ± 4.74 | 124 ± 40 | 538 ± 274 | >10000 |
| L858R + T790M + L792Y | 11.3 ± 5.8 | 273 ± 72 | 512 ± 269 | >10000 |

The invention claimed is:

1. A method for treating a patient having lung cancer, comprising administering(S)—N-(4-amino-6-methyl-5-(quinolin-3-yl)-8,9-dihydropyrimido[5,4-b]indolizin-8-yl) acrylamide, as Compound (A), or a salt thereof to the patient expressing EGFR having at least one mutation selected from the group consisting of L718X mutation in exon 18 and L792X mutation in exon 20.

2. The method according to claim 1, wherein the EGFR further has at least one mutation selected from the group consisting of exon 19 deletion mutations L858R, L861Q, G719X, E709X, and an exon 20 insertion mutation.

3. The method according to claim 2, wherein the EGFR further has a T790M mutation.

4. The method according to claim 1, wherein the L718X mutation is a L718Q mutation.

5. The method according to claim 1, wherein the L792X mutation is L792H, L792F, or L792Y.

6. The method according to claim 1, wherein the(S)—N-(4-amino-6-methyl-5-(quinolin-3-yl)-8,9-dihydropyrimido[5,4-b]indolizin-8-yl) acrylamide or a salt thereof is administered to the patient in a form of a pharmaceutical composition further comprising a pharmaceutically acceptable carrier.

* * * * *